US012048891B2

(12) United States Patent
Yatsunami et al.

(10) Patent No.: US 12,048,891 B2
(45) Date of Patent: Jul. 30, 2024

(54) MULTILAYER FILTER MATERIAL

(71) Applicant: Toray Industries, Inc., Tokyo (JP)

(72) Inventors: Yuji Yatsunami, Otsu (JP); Yasuhiro Asada, Otsu (JP); Yufuko Takaki, Otsu (JP)

(73) Assignee: Toray Industries, Inc., Tokyo (JP)

( * ) Notice: Subject to any disclaimer, the term of this patent is extended or adjusted under 35 U.S.C. 154(b) by 791 days.

(21) Appl. No.: 17/041,502

(22) PCT Filed: Mar. 28, 2019

(86) PCT No.: PCT/JP2019/013746
§ 371 (c)(1),
(2) Date: Sep. 25, 2020

(87) PCT Pub. No.: WO2019/189638
PCT Pub. Date: Oct. 3, 2019

(65) Prior Publication Data
US 2021/0046410 A1    Feb. 18, 2021

(30) Foreign Application Priority Data

Mar. 30, 2018  (JP) ................................. 2018-067922

(51) Int. Cl.

| B01D 46/00 | (2022.01) |
|---|---|
| A61L 9/014 | (2006.01) |
| B01D 39/16 | (2006.01) |
| B01D 46/10 | (2006.01) |
| B01D 53/44 | (2006.01) |
| B01D 53/72 | (2006.01) |
| B01D 53/81 | (2006.01) |
| B01J 21/08 | (2006.01) |
| B01J 31/02 | (2006.01) |
| B01J 35/00 | (2006.01) |
| B01J 35/50 | (2024.01) |
| B01J 35/58 | (2024.01) |
| B01J 37/02 | (2006.01) |
| B32B 5/02 | (2006.01) |
| B32B 5/16 | (2006.01) |
| B32B 5/30 | (2006.01) |

(52) U.S. Cl.
CPC .......... *B01D 46/0038* (2013.01); *A61L 9/014* (2013.01); *B01D 39/16* (2013.01); *B01D 46/0001* (2013.01); *B01D 46/0032* (2013.01); *B01D 46/0036* (2013.01); *B01D 46/10* (2013.01); *B01D 53/44* (2013.01); *B01D 53/72* (2013.01); *B01D 53/81* (2013.01); *B01J 21/08* (2013.01); *B01J 31/0209* (2013.01); *B01J 35/19* (2024.01); *B01J 35/50* (2024.01); *B01J 35/58* (2024.01); *B01J 37/0215* (2013.01); *B32B 5/022* (2013.01); *B32B 5/16* (2013.01); *B32B 5/30* (2013.01); *A61L 2209/14* (2013.01); *A61L 2209/22* (2013.01); *B01D 2239/0407* (2013.01); *B01D 2239/0435* (2013.01); *B01D 2239/045* (2013.01); *B01D 2239/0618* (2013.01); *B01D 2239/065* (2013.01); *B01D 2239/10* (2013.01); *B01D 2239/1241* (2013.01); *B01D 2253/304* (2013.01); *B01D 2257/708* (2013.01); *B01D 2275/10* (2013.01)

(58) Field of Classification Search
None
See application file for complete search history.

(56) References Cited

U.S. PATENT DOCUMENTS

| 5,605,746 A * | 2/1997 | Groeger ............. D04H 1/43838 428/359 |
|---|---|---|
| 2006/0096910 A1 | 5/2006 | Brownstein et al. |
| 2008/0148946 A1* | 6/2008 | Lotgerink-Bruinenberg ............... B01D 39/163 96/55 |
| 2009/0261032 A1 | 10/2009 | Gohle et al. |
| 2010/0212506 A1 | 8/2010 | Togashi et al. |
| 2011/0240027 A1 | 10/2011 | Billingsley et al. |
| 2014/0013957 A1 | 1/2014 | Scope et al. |

(Continued)

FOREIGN PATENT DOCUMENTS

| JP | 49134783 U | 11/1974 |
|---|---|---|
| JP | 11300126 A | 11/1999 |
| JP | 2000-070645 A | 3/2000 |

(Continued)

OTHER PUBLICATIONS

JP2002177717A—translated document (Year: 2002).*

(Continued)

*Primary Examiner* — Jelitza M Perez

(74) *Attorney, Agent, or Firm* — Buchanan Ingersoll & Rooney PC

(57) ABSTRACT

The challenge of the present invention is to provide a multilayer filter medium whose deodorizing performance after a long-term storage of the filter medium is suppressed from deteriorating and which is superior in deodorizing performance and exhibits low pressure drop. A multilayer filter medium includes three or more nonwoven fabric layers superposed together and has two or more interlayer regions each formed by two adjacent layers of the nonwoven fabric layers, in which a first interlayer region of the interlayer regions contains functional particles A having an average particle diameter of 50 to 100 μm, and a second interlayer region selected from the interlayer regions excluding the first interlayer region contains functional particles B having an average particle diameter of 150 to 500 μm.

11 Claims, No Drawings

(56) References Cited

U.S. PATENT DOCUMENTS

2015/0053080 A1 2/2015 Boehringer et al.
2017/0320001 A1 11/2017 Stinzendoerfer et al.

FOREIGN PATENT DOCUMENTS

| JP | 2000233111 A | | 8/2000 |
|---|---|---|---|
| JP | 2002-085536 A | | 3/2002 |
| JP | 2002177717 A | * | 6/2002 |
| JP | 2002177717 A | | 6/2002 |
| JP | 2002331212 A | | 11/2002 |
| JP | 2003334410 A | | 11/2003 |
| JP | 2007136029 A | | 6/2007 |
| JP | 2011-072911 A | | 4/2011 |
| JP | 2012-512742 A | | 6/2012 |
| JP | 2015-062860 A | | 4/2015 |
| JP | 2015139720 A | | 8/2015 |
| WO | 2009041257 A1 | | 4/2009 |

OTHER PUBLICATIONS

Indian Examination Report for Indian Application No. 202047046601, dated May 20, 2022, with translation, 6 pages.
Extended European Search Report for European Application No. 19 778 338.4, dated Nov. 25, 2021, 8 pages.
International Search Report and Written Opinion for International Application No. PCT/JP2019/013746, dated Jul. 2, 2019, with partial translation, 5 pages.
Office Action (Notice of Reasons for Refusal) issued Feb. 7, 2023, by the Japan Patent Office in corresponding Japanese Patent Application No. 2019-517438 and an English translation of the Office Action. (8 pages).
Office Action (Request for the Submission of an Opinion) issued Apr. 25, 2024, by the Korean Intellectual Property Office in corresponding Korean Patent Application No. 10-2020-7027302 and an English translation of the Office Action. (13 pages).

* cited by examiner

MULTILAYER FILTER MATERIAL

CROSS REFERENCE TO RELATED APPLICATIONS

This is the U.S. National Phase application of PCT/JP2019/013746, filed Mar. 28, 2019, which claims priority to Japanese Patent Application No. 2018-067922, filed Mar. 30, 2018, the disclosures of each of these applications being incorporated herein by reference in their entireties for all purposes.

FIELD OF THE INVENTION

The present invention relates to a multilayer filter medium suitable for an air filter.

BACKGROUND OF THE INVENTION

In recent years, interest in human health due to pollutants in the air has increased, and attention has been attracted to the quality of indoor air. There are various types of pollutants such as dust and odor, and in order to remove them, air cleaners having not only dust removal but also deodorizing performance are widely used.

As a filter medium to be used for an air filter having deodorizing performance, it is known that functional particles having a deodorizing function arranged in an interlayer region located between two nonwoven fabric layers in the interlayer region located between the two nonwoven fabric layers (for example, see Patent Document 1).

Further, as functional particles having a deodorizing function, silica particles to which a hydrazine compound is impregnated are known. From the viewpoint of suppressing deterioration of the deodorizing performance of the filter medium after long-term storage of the filter medium, it is effective to use functional particles having a large particle diameter. On the other hand, as disclosed in Patent Document 2, it is known that it is effective to use functional particles having a small particle diameter from the viewpoint of improving the deodorizing performance of the filter medium.

PATENT DOCUMENTS

Patent Document 1: Japanese Patent Laid-open Publication No. 2015-139720
Patent Document 2: Japanese Patent Laid-open Publication No. 2007-136029

SUMMARY OF THE INVENTION

Considering the matters described in Patent Document 2, in order to obtain a filter medium that can suppress the deterioration of the deodorizing performance of the filter medium after long-term storage of the filter medium and is superior in deodorizing performance, for example, it is conceivable that in the filter medium disclosed in Patent Document 1, functional particles having a larger particle diameter and functional particles having a smaller particle diameter are arranged in the interlayer region between two nonwoven fabric layers.

According to the knowledge of the present inventor, in this case, there is a problem that the pressure drop of the air filter using this filter medium becomes higher, and this filter medium becomes unsuitable for the air filter applications.

Therefore, in view of the above circumstances, it is a challenge of the present invention to provide a multilayer filter medium whose deodorizing performance after long-term storage of the filter medium is suppressed from deteriorating and which is superior in deodorizing performance and exhibits low pressure drop.

The present invention according to exemplary embodiments is a multilayer filter medium that employs the following configurations in order to meet such a challenge.

(1) A multilayer filter medium including three or more nonwoven fabric layers superposed together and having two or more interlayer regions each formed by two adjacent layers of the nonwoven fabric layers, in which a first interlayer region of the interlayer regions contains functional particles A having an average particle diameter of 50 to 100 μm, and a second interlayer region selected from the interlayer regions excluding the first interlayer region contains functional particles B having an average particle diameter of 150 to 500 μm.

(2) The multilayer filter medium, in which a basis weight of the functional particles A in the first interlayer region is 20 to 80 g/m2, and a basis weight of the functional particles B in the second interlayer region is 20 to 600 g/m2.

(3) Any one of the above-described multilayer filter media, in which one of the functional particles A and the functional particles B are functional particles having acidic gas adsorption capability, and the other of the functional particles A and the functional particles B are functional particles having basic gas adsorption capability.

(4) Any one of the above-described multilayer filter media, in which at least one layer of the three or more nonwoven fabric layers is charged nonwoven fabric.

(5) Any one of the above-mentioned multilayer filter media which has a collection efficiency of 99.97% or more for particles having an average particle diameter of 0.3 μm.

(6) Any one of the above-mentioned multilayer filter media, in which at least one of the functional particles A and the functional particles B chemically adsorb volatile organic compound gas.

(7) Any one of the above-mentioned multilayer filter media, in which at least one of the functional particles A and the flat functional particles B selectively and chemically adsorb aldehyde gas.

(8) An air filter including any one of the above-mentioned multilayer filter media.

(9) A method for manufacturing any one of the above-mentioned multilayer filter media, including:

a step of arranging the functional particles A on the surface of a first nonwoven fabric layer selected from among the nonwoven fabric layers;

a step of arranging the functional particles B on the surface of a second nonwoven fabric layer selected from among the nonwoven fabric layers; and a step of superposing three or more nonwoven fabric layers.

According to the present invention, it is possible to provide a multilayer filter medium whose deodorizing performance after a long-term storage of the filter medium is suppressed from deteriorating and which is superior in deodorizing performance and exhibits low pressure drop.

DETAILED DESCRIPTION OF EMBODIMENTS OF THE INVENTION

The multilayer filter medium according to embodiments of the present invention has three or more nonwoven fabric layers, and has two or more interlayer regions formed by two adjacent nonwoven fabric layers. In addition, a first interlayer region of the two or more interlayer regions contains functional particles having an average particle diameter of 50 to 100 μm (hereinafter referred to as functional particles A), and a second interlayer region of the two or more interlayer regions contains functional particles having an average particle diameter of 150 to 500 μm (hereinafter referred to as functional particles B).

That is, the functional particles A are arranged in the first interlayer region provided in the multilayer filter medium according to embodiments of the present invention, and the functional particles B are arranged in the second interlayer region provided in the multilayer filter medium according to embodiments of the present invention. Since the functional particles A and the functional particles B are separately arranged in different interlayer regions provided in the multilayer filter medium according to embodiments of the present invention as described above, the deterioration of the deodorizing performance of the multilayer filter medium of the present invention after a long-term storage of the filter medium is suppressed, the filter medium is superior in deodorizing performance, and the pressure drop of the filter medium is low.

The reason why the above effects are exhibited with the multilayer filter medium according to embodiments of the present invention is considered as follows. In order to obtain a multilayer filter medium with which deterioration of the deodorizing performance after long-term storage of the filter medium is suppressed and which is superior in deodorizing performance, the functional particles A and the functional particles B are used. However, when the functional particles A and B are arranged in the same interlayer region of the multilayer filter medium, the pressure drop of an air filter including this multilayer filter medium is high. This is expected to be because the functional particles A having a smaller particle diameter and the functional particles B having a larger particle diameter are mixed in one interlayer region of the multilayer filter medium, so that the arrangement of the functional particles A and B is as follows. That is, thanks to the functional particles B being located in the one interlayer region, the one interlayer region has a large thickness and has a low density. And, thanks to the condition that the functional particles A are further located in the one interlayer region, the functional particles A enter gaps formed by the plurality of functional particles B, so that the one interlayer region has a large thickness, and the functional particles A and B are densely filled. Then, it is considered that when airflow is performed through a multilayer filter medium having such one interlayer region, such one interlayer region has low air permeability, and as a result, the pressure drop of the multilayer filter medium is high.

Hereinafter, details of materials to be used for the multilayer filter medium according to embodiments of the present invention and details of the configuration of the multilayer filter medium according to embodiments of the present invention will be described.

Functional Particles

First, the functional particles are described. Specific examples of the functional particles that can be used in the present invention include activated carbon particles, silicon dioxide particles, zeolite particles, activated alumina particles, activated clay particles, aluminum silicate particles, magnesium silicate particles, ion-exchange resin particles, and these particles to which the chemicals described below are impregnated. These kinds of particles may be used alone or in combination. Among these kinds of particles, activated carbon particles, silicon dioxide particles, zeolite particles, and these particles to which the chemicals described below are impregnated are superior in the ability to adsorb volatile organic compound (VOC) gas such as aldehyde gas and are suitably used as a gas adsorbent in the multilayer filter medium according to embodiments of the present invention. Further, as will be described in detail later, the reason why the multilayer filter medium has an improved deodorizing performance is that the functional particles are activated carbon particles, silicon dioxide particles, or zeolite particles to which the chemicals described below are affixed. It is preferable that these particles are porous bodies because the deodorizing performance of the multilayer filter medium will be more improved. As described above, activated carbon particles, silicon dioxide particles or the like may be used in combination as the functional particles. Therefore, for example, functional particles composed of activated carbon particles and silicon dioxide particles and having an average particle diameter of 50 to 100 μm as a whole serve as the functional particle A.

Average Particle Diameter of Functional Particles

In embodiments of the multilayer filter medium of the present invention, two or more kinds of functional particles differing in average particle diameter are used, and since the functional particles A have a larger surface area per volume and higher in efficiency of contact with gas, the multilayer filter medium according to embodiments of the present invention having this kind of functional particles are particularly superior in deodorizing performance. On the other hand, since the functional particles B have a smaller surface area per volume and are lower in efficiency of contact with air, which promotes the deterioration with time of the gas adsorption performance of the functional particles, the deterioration of the deodorizing performance of the multilayer filter medium of the present invention containing this kind of functional particles after long-term storage of the filter medium can be suppressed.

The multilayer filter medium containing the functional particles A and the functional particles B has superior deodorizing performance and can suppress deterioration of its deodorizing performance resulting from a long-term storage thereof.

Here, the average particle diameter of the functional particles A is 50 to 100 μm. If the average particle diameter of the functional particles A is less than 50 μm, the multilayer filter medium has a high rate of adsorbing gas to be adsorbed, but according to the pore size of the nonwoven fabric layer of the multilayer filter medium, the functional particles A tend to fall off from the multilayer filter medium. In addition, if the average particle diameter of the functional particles A is less than 50 μm, the handleability and the processability of the functional particles A tend to deteriorate. On the other hand, if the average particle diameter of the functional particles A is more than 100 μm, the surface area of the functional particles A versus the volume of the functional particles A is small, so that the functional particles A have a decreased rate of adsorbing gas to be adsorbed, and the deodorizing performance tends to deteriorate. Next, the average particle diameter of the functional particles B is 150 to 500 μm. If the average particle diameter of the functional particles B is less than 150 μm, the multilayer filter medium has an increased rate of adsorbing gas to be absorbed, and especially, when the functional particles B are those in which a chemical is affixed to silicon dioxide particles or the like, the performance of adsorbing a target gas deteriorates with time as a result of contact with air, so that the duration of the deodorizing performance tends to be shortened. On the other hand, when the average particle diameter of the functional particles B is more than 500 μm, functional particles B sandwiched between filter media when pleating the filter media tend to break through nonwoven fabric layers, and functional particles tend to be crushed during the pleating or the like. When the functional particles are crushed, a fine powder of the functional particles whose diameter are as small as 50 μm or less tend to be generated.

Here, the average particle diameter of the functional particles was measured by a technique that involves observing using an SEM (scanning electron microscope) and measuring the size of each particle directly from the observed image. Specifically, the average particle diameter was determined as follows.

The functional particles to be measured are observed by SEM. The field of view is set at random. In the observation field of view, all particles whose contour showing the whole image of the particle can be grasped (that is, all particles excluding particles whose contour cannot be grasped because part of the particle is blocked by other particles or protrudes out of the field of view) are selected. For each of the particle selected by this method, the projected area S of the particle is determined from the contour of the particle in the SEM image. The projected area S can be measured using image processing. The diameter D of a circle having an area equal to the projected area S is defined as the equivalent circle diameter D of the particle. The measurement is repeated until the total number of selected particles reaches 200 or more. The value obtained by dividing the sum of the equivalent circle diameters D by the total number N of the selected particles is defined as the average particle diameter.

The functional particles of the present invention preferably have a narrow particle size distribution. For example, the coefficient of variation CV defined by the following equation is preferably 0.7 or less, and more preferably 0.5 or less.

$$CV = \sigma D / D50$$

Here, $\sigma D$ is the standard deviation of the equivalent circle diameters of the functional particles, and D50 is the average particle diameter of the functional particles.

Basis Weight of Functional Particles

Next, the basis weight of the functional particles A and the basis weight of the functional particles B in the multilayer filter medium according to embodiments of the present invention are described. Here, the basis weight of functional particles refers to the basis weight of the functional particles in one of the plurality of interlayer regions of the multilayer body.

In embodiments of the present invention, the functional particles A and the functional particles B are separately arranged in different interlayer regions. In addition, thanks to the configuration described above, the multilayer filter medium of the present invention can suppress deterioration of the deodorizing performance of the multilayer filter medium after long-term storage, and is superior in the deodorizing performance of the filter medium, and the pressure drop of the multilayer filter medium is low. The basis weights of the functional particles A and the functional particles B, which are separately arranged in the different interlayer regions, each have a suitable range. When the functional particles A and the functional particles B are separately arranged in two or more interlayer regions within the suitable range of the basis weights described later, the above-mentioned effects of the present invention become more remarkable.

The preferable ranges of the basis weights of the functional particles A and the functional particles B are described below.

The basis weight of the functional particles A is preferably in the range of 20 $g/m^2$ to 80 g/m2. The basis weight of the functional particles A is more preferably 30 g/m2 or more. The basis weight of the functional particles A is more preferably 60 $g/m^2$ or less. Thanks to setting the basis weight of the functional particles A to 20 $g/m^2$ or more, the filter medium is superior in deodorizing performance and the deodorizing performance of the filter medium after long-term storage can be suppressed from deteriorating. Further, thanks to setting the basis weight of the functional particles A to 80 $g/m^2$ or less, the multilayer filter medium has particularly superior air permeability and the increase of pressure drop can be further suppressed.

The basis weight of the functional particles B is preferably in the range of 20 g/m2 to 600 g/m2. The basis weight of the functional particles B is more preferably 100 $g/m^2$ or more. The basis weight of the functional particles B is preferably 500 g/m2 or less. Thanks to setting the basis weight of the functional particles B to 20 $g/m^2$ or more, the filter medium is superior in initial deodorizing performance and the deodorizing performance of the filter medium after long-term storage can be suppressed from deteriorating. Thanks to setting the basis weight of the functional particles B to 600 $g/m^2$ or less, the air permeability of the multilayer filter medium is particularly superior, so that the increase of pressure drop can be further suppressed, and the multilayer filter medium is bulky, so that when the filter medium is subjected to pleating or the like, it is possible to suppress the difference between the inner diameter and the outer diameter of the filter medium from increasing, and therefore the occurrence of tearing can be suppressed.

Pore Diameter of Functional Particles

For the purpose of efficiently removing gas, the pore diameter of the functional particles A to be used in exemplary embodiments of the present invention is preferably 0.5 to 100 nm. Thanks to the pore diameter of the functional particles A being 100 nm or less, the specific surface area of the functional particles A becomes large and high deodorizing performance can be realized. Further, owing to the pore diameter of the functional particles A being 0.5 nm or more, the penetration of the gas component to be removed into the pores is promoted. The pore diameter of the functional particles B to be used in the present invention is preferably 0.5 nm or more. Thanks to the pore diameter of the functional particles B being 0.5 nm or more, the penetration of the gas component to be removed into the pores is promoted. Regarding the pore diameter of functional particles, the shape of the pores is assumed to be cylindrical, and the pore diameter is calculated as an average pore diameter (D) by the following equation from the BET specific surface area (S) described later and the pore volume (V) obtained during the BET specific surface area measurement.

$$D = 4V/S$$

Specific Surface Area of Functional Particles

The larger the specific surface area of the functional particles to be used in the present invention, the more preferable in terms of deodorizing performance.

For example, the specific surface area of the functional particles A is preferably a BET specific surface area of 50 m²/g or more. Owing to the BET specific surface area of the functional particles A being 50 m²/g or more, it is possible to secure an effective area where the target gas to be removed and the functional particles A are in contact, and the rate of removing the gas to be removed by the functional particles A becomes higher. When the functional particles are non-porous, the deodorizing performance can be improved by reducing the particle diameter of the functional particles A because the geometric surface area can thereby be increased and the contact area can be secured.

The specific surface area of the functional particles B to be used in the present invention is preferably a BET specific surface area of 50 to 2000 m2/g. Owing to the BET specific surface area of the functional particles B being 50 m²/g or more, it is possible to secure an effective area where the gas component to be removed and the functional particles B are in contact, and the rate of removing the gas to be removed by the functional particles B becomes higher. Owing to the BET specific surface area of the functional particles B being 2000 m²/g or less, the deodorizing performance of the functional particles B after long-term storage can be suppressed from deteriorating because of low efficiency of contact with air, that promotes the deterioration with time of the gas adsorption performance.

Chemicals

As described above, one form of the functional particles may be particles such as silicon dioxide particles to which a chemical is affixed. The above-mentioned chemicals are described below.

Gases which are difficult to be removed by physical adsorption to functional particles can be chemically removed by using the functional particles in which chemical is carried on silicon dioxide particles or the like. As the chemical, for example, acid dihydrazide compounds for removing aldehyde gas, metal carbonates for acidic gas removal, and acidic compounds for basic gas removal are suitable.

Examples of the acid dihydrazides include acid monohydrazides having one acid hydrazide group in the molecule, such as formhydrazide, acetohydrazide, propionic acid hydrazide, and benzoic acid hydrazide, acid dihydrazides having two acid hydrazide groups in the molecule, such as oxalic acid dihydrazide, malonic acid dihydrazide, succinic acid dihydrazide, adipic acid dihydrazide, fumaric acid dihydrazide, maleic acid dihydrazide, and terephthalic acid dihydrazide, and acid polyhydrazides having three or more acid hydrazide groups in the molecule, such as polyacrylic acid hydrazide. Of these, dihydrazides are preferable, and adipic acid dihydrazide is particularly preferable in terms of aldehyde adsorption performance.

The acid hydrazide compounds are compounds having an acid hydrazide group represented by —CO—NHNH2 derived from a carboxylic acid and hydrazine, and a nitrogen atom having an lone pair is further bonded to the α-position of the hydrazide terminal, which significantly improves the nucleophilic reactivity. The lone pair reacts by nucleophilically attacking the carbonyl carbon atom of the aldehydes and forms chemical bond with the aldehydes as a hydrazine derivative, whereby the aldehyde removal performance can be exhibited.

The amount of the acid dihydrazide compound carried on the functional particles to be used in the multilayer filter medium of the present invention is preferably 1 to 50 parts by mass per 100 parts by mass of the functional particles. The lower limit is preferably 3 parts by mass or more, and the upper limit is preferably 30 parts by mass or less. Owing to the carried amount being 1 part by mass or more, the efficiency of removing aldehydes and the effective adsorption capacity can be obtained. Owing to the carried amount being 50 parts by mass or less, the acid dihydrazide compound on the functional particles can be suppressed from crystallizing and the pores of the functional particles are suppressed from being closed by the acid dihydrazide compound crystallized, whereby the functional particles can be suppressed from decreasing in gas adsorption rate. Furthermore, the carried amount is preferably 50 parts by mass or less because the carried amount being 50 parts by mass or more causes the chemical to fall off from the functional particles.

The pH of the interlayer region containing the functional particles on which the acid dihydrazide compound is carried is preferably in the range of 3.0 to 7.5. Owing to the pH of the interlayer region being 7.5 or less, the intermediate produced from the reaction by the nucleophilic attack on the carbonyl carbon atom of the aldehydes by the unshared electron pair of the acid hydrazide compound is protonated in the acidic reaction field, whereby the intermediate becomes easy to be dehydrated, so that the forming chemical bond to the derivative proceeds sufficiently. That is, owing to the pH of the interlayer region being 7.5 or less, the decomposition of the aldehydes by the acid hydrazide compound is further promoted. Thanks to the pH of the interlayer region being 3.0 or more, the activity of the unshared electron pair of the acid hydrazide compound to nucleophilically attack the carbonyl carbon atom of the aldehydes can be sufficiently maintained. That is, also owing to the pH of the interlayer region being 3.0 or more, the decomposition of the aldehydes by the acid hydrazide compound is further promoted. The pH of the interlayer region is a value determined as follows. The gas adsorbent arranged in the interlayer region is immersed in pure water at 25° C. such that the concentration of the gas absorbent is 5% by mass, followed by lightly stirring and subsequently allowing to stand for 10 minutes, and then the pH of the resulting supernatant is measured with a pH meter. The measurement is performed three times and the average value is used.

Here, functional particles carrying a metal carbonate for the acidic gas removal described below, or functional particles carrying an acidic compound for the basic gas removal described below tend to change the pH of the interlayer region. As described above, the aldehydes removal performance of the acid hydrazide compound is affected by the pH of the interlayer region. Therefore, the multilayer filter medium of the present invention preferably has the functional particles carrying the acid dihydrazide compound and the functional particles carrying the metal carbonate for acidic gas removal in different interlayer regions of the multilayer filter medium, respectively.

As the metal carbonate for acidic gas removal, for example, alkali metal carbonates, such as potassium carbonate, potassium hydrogen carbonate, sodium carbonate, and sodium hydrogen carbonate, are suitably used. As the acidic compound for basic gas removal, for example, phosphoric acid, sulfuric acid, nitric acid, malic acid, and ascorbic acid are suitably used.

The carried amount of the metal carbonate in the functional particles to be used in the multilayer filter medium of the present invention is preferably 1 to 20 parts by mass per 100 parts by mass of the functional particles. The upper limit is more preferably 10 parts by mass or less. Thanks to the carried amount being 1 part by mass or more, the acidic gas removal efficiency by the functional particles is more improved and the acidic gas adsorption capacity of the functional particles is also more enhanced. On the other hand, when the acidic gas removing compound is added in excess, pores of the functional particles are closed, so that the adsorption rate decreases or the chemical falls off from the functional particles. Therefore, the carried amount is preferably set to 10 parts by mass or less. The carried amount of the acidic compound in the functional particles to be used in the multilayer filter medium of the present invention is preferably 1 to 20 parts by mass per 100 parts by mass of the functional particles. The upper limit is more preferably 10 parts by mass or less. Owing to the carried amount being 1 part by mass or more, the basic gas removal efficiency by functional particles is more improved and the basic gas adsorption capacity of the functional particles is also more enhanced. On the other hand, when the acidic compound is added in excess, pores of the functional particles are blocked, so that the adsorption rate decreases or the powder falls off. Therefore, the added amount is preferably set to 10 parts by mass or less.

The functional particles carrying a metal carbonate for acidic gas removal and the functional particles carrying an acidic compound for basic gas removal, which are arranged in the same interlayer region of the multilayer filter medium, tend to mutually reduce their gas removal performance. This is considered to be due to a neutralization reaction. From the above, the multilayer filter medium of the present invention is preferably one containing the functional particles carrying a metal carbonate for acidic gas removal and the functional particles carrying an acidic compound for basic gas removal in different interlayer regions of the multilayer filter medium, respectively. Specifically, in the multilayer filter medium of the present invention, it is preferable that one of the functional particles A and the functional particles B be functional particles having acidic gas adsorption capability, and the other of the functional particles A and the functional particles B be functional particles having basic gas adsorption capability.

Configuration of Filter Medium

While the multilayer filter medium according to embodiments of the present invention has three or more nonwoven fabric layers, at least one of the three or more nonwoven fabric layers can be preferably formed of charged nonwoven fabric because the dust collection performance of the multilayer filter medium can thereby be made superior.

Electret Nonwoven Fabric Layer

Preferably, at least one nonwoven fabric layer of the nonwoven fabric layers constituting the multilayer filter medium of the present invention is electretized. Use of the electretized nonwoven fabric layer makes it possible to perform not only physical collection of dust to the fibers of the nonwoven fabric layer, but also electrostatic collection, so that a collection efficiency of 99.97% or more with respect to particles having an average particle diameter of 0.3 μm can be achieved more easily with low pressure drop.

As the material to form the electret-treated nonwoven fabric layer, namely, the charged nonwoven fabric, materials having high electric resistivity such as synthetic polymer materials, such as polyolefin resins, such as polypropylene, polyethylene, polystyrene, polybutylene terephthalate, and polytetrafluoroethylene, aromatic polyester resins, such as polyethylene terephthalate, and polycarbonate resins, are preferable.

Method for Manufacturing Multilayer Filter Medium

Examples of the method for manufacturing the multilayer filter medium of the present invention include the following. Specifically, it is a method for manufacturing a multilayer filter medium, including step I of arranging functional particles A on the surface of a first nonwoven fabric layer selected from among the nonwoven fabric layers to be used in exemplary embodiments of the present invention, step II of arranging functional particles B on the surface of other three or more nonwoven fabric layers a second nonwoven fabric layer, and step III of superposing three or more nonwoven fabric layers.

EXAMPLES

Measurement Methods (1) Collection Efficiency [%]

A flat filter medium is set in a holder with an effective inlet area of 0.01 m2, and air is passed vertically there through at a surface wind velocity of 4.5 m/min. The number of air dust particles with a particle diameter of 0.3 to 0.5 μm is counted on the upstream side and the downstream side of the filter by using a particle counter (manufactured by RION Co., Ltd., model: KC-01D), and a collection efficiency is calculated using the following equation.

Collection efficiency (%)=1−(number of downstream particles/number of upstream particles)×100.

This measurement is made on five samples arbitrarily taken out of each specimen, and the average value thereof is used.

(2) Pressure Drop [Pa]

A flat filter medium is set in a holder with an effective inlet area of 0.01 m2, air is passed vertically there through at a surface wind velocity of 4.5 m/min, and the difference in pressure between the upstream side and the downstream side of the filter is measured with a digital manometer MA2-04P differential pressure gauge manufactured by MODUS. This measurement is made on five samples arbitrarily taken out of each specimen, and the average value thereof is used.

(3) Carried Amount of Chemical [%]

Functional particles were impregnated with an aqueous solution of a chemical, followed by drying. The total carried amount was calculated from the difference between the weight of the functional particles after the impregnation and the drying and the weight of the functional particles before the impregnation and the drying. The total carried amount was multiplied by the proportion of respective components and thereby converted to their carried amounts relative to the functional particles, and thus the carried amount of the chemical is calculated.

(4) Acetaldehyde Removal Efficiency [%] and Acetaldehyde Adsorption Capacity [g/m2]

A 12 cm square flat filter media prepared in each of the examples and comparative examples is attached to a 10 cm square experimental duct, and air with a temperature of 23° C. and a humidity of 50% RH is blown into the duct at a speed of 0.2 m/sec. Further, acetaldehyde is added at the upstream end from a standard gas cylinder at an upstream concentration of 10 ppm and the air is sampled on the upstream and downstream sides of the filter medium. The change in the acetaldehyde concentration with time is measured on each side using an infrared absorption type continuous monitor and the removal efficiency is calculated using the following equation.

$$\text{Removal efficiency (\%)} = [(C0 - C)/C0] \times 100$$

Here, C0 is the acetaldehyde concentration on the upstream side (=10 ppm), and

C is the acetaldehyde concentration (ppm) on the downstream side.

The removal efficiency is measured 2 minutes after the start of the acetaldehyde addition to determine the initial removal efficiency and the change in removal efficiency with time is measured after this 2 minutes point. In addition, the amount adsorbed until the time when the difference between the upstream side concentration and the downstream side concentration reaches 5% is evaluated. The adsorbed amount per unit m2 of the filter medium (=adsorption capacity [g/m$^2$]) is calculated by dividing the adsorbed amount by the filter medium area (10 cm square) used for the evaluation of the acetaldehyde gas deodorizing performance.

(5) Acetic Acid Removal Efficiency [%] and Acetic Acid Adsorption Capacity [g/m$^2$]

A 12 cm square flat filter media prepared in each of the examples and comparative examples is attached to a 10 cm square experimental duct, and air with a temperature of 23° C. and a humidity of 50% RH is blown into the duct at a speed of 0.2 m/sec. Further, acetic acid gas is added at the upstream end from a standard gas cylinder at an upstream concentration of 10 ppm and the air is sampled on the upstream and downstream sides of the filter medium. The change in the acetic acid concentration with time is measured on each side using an infrared absorption type continuous monitor and the removal efficiency is calculated using the following equation.

$$\text{Removal efficiency (\%)} = [(C0 - C)/C0] \times 100$$

Here, C0 is the acetic acid concentration on the upstream side (=10 ppm), and

C is the acetic acid concentration (ppm) on the downstream side.

The removal efficiency is measured 2 minutes after the start of the acetic acid addition to determine the initial removal efficiency and the change in removal efficiency with time is measured after this 2 minutes point. In addition, the amount adsorbed until the time when the difference between the upstream side concentration and the downstream side concentration reaches 5% is evaluated. The adsorbed amount per unit m$^2$ of the filter medium (=adsorption capacity [g/m$^2$]) is calculated by dividing the adsorbed amount by the filter medium area (10 cm square) used for the evaluation of the acetic acid gas deodorizing performance.

(6) Ammonia Removal Efficiency [%] and Ammonia Adsorption Capacity [g/m2]

A 12 cm square flat filter media prepared in each of the examples and comparative examples is attached to a 10 cm square experimental duct, and air with a temperature of 23° C. and a humidity of 50% RH is blown into the duct at a speed of 0.2 m/sec. Further, ammonia is added at the upstream end from a standard gas cylinder at an upstream concentration of 10 ppm and the air is sampled on the upstream and downstream sides of the filter medium. The change in the acetic acid concentration with time is measured on each side using an infrared absorption type continuous monitor and the removal efficiency is calculated using the following equation.

$$\text{Removal efficiency (\%)} = [(C0 - C)/C0] \times 100$$

Here, C0 is the ammonia concentration on the upstream side (=10 ppm), and

C is the ammonia concentration (ppm) on the downstream side.

The removal efficiency is measured 2 minutes after the start of the ammonia addition to determine the initial removal efficiency and the change in removal efficiency with time is measured after this 2 minutes point. In addition, the amount adsorbed until the time when the difference between the upstream side concentration and the downstream side concentration reaches 5% is evaluated. The adsorbed amount per unit m2 of the filter medium (=adsorption capacity [g/m$^2$]) is calculated by dividing the adsorbed amount by the filter medium area (10 cm square) used for the evaluation of the ammonia gas deodorizing performance.

(7) Toluene Removal Efficiency [%] and Toluene Adsorption Capacity [g/m$^2$]

A 12 cm square flat filter media prepared in each of the examples and comparative examples is attached to a 10 cm square experimental duct, and air with a temperature of 23° C. and a humidity of 50% RH is blown into the duct at a speed of 0.2 m/sec. Further, toluene is added at the upstream end from a standard gas cylinder at an upstream concentration of 80 ppm and the air is sampled on the upstream and downstream sides of the sheet medium. The change in the toluene concentration with time is measured on each side using an infrared absorption type continuous monitor and the toluene deodorization efficiency is determined therefrom.

$$\text{Deodorization efficiency (\%)} = [(C0 - C)/C0] \times 100$$

Here, C0 is the toluene concentration on the upstream side (=80 ppm), and

C is the toluene concentration (ppm) on the downstream side.

The deodorization efficiency is measured 2 minutes after the start of the toluene addition to determine the initial deodorization efficiency and the change in removal efficiency with time is measured after this 2 minutes point. In addition, the amount adsorbed until the time when the difference between the upstream side concentration and the downstream side concentration reaches 5% is evaluated. The adsorbed amount per unit m2 of the filter medium (=adsorption capacity [g/m$^2$]) is calculated by dividing the adsorbed amount by the filter medium area (10 cm square) used for the evaluation of the toluene gas deodorizing performance.

(8) Average Particle Diameter [μm] of Functional Particles Contained in Multilayer Filter Medium A nonwoven fabric layer of a multilayered filter medium is isolated, and functional particles on the nonwoven fabric layer in a visual field with a size of 1700 μm by 1300 μm are observed at a 200 magnification and a 1600- by 1200-pixel resolution by using an optical microscope (digital macroscope (model VHX-6000 manufactured by KEYENCE Corporation)). The equivalent circle diameter and the coefficient of variation CV value were determined by the methods described above.

(9) Basis Weight [g/m$^2$]

A mixed powder 1 prepared by mixing and stirring functional particles 1 and an additive 1 such as a thermoplastic resin (binder) is scattered onto a nonwoven fabric layer 1 (area: 1 m2), then another nonwoven fabric layer 2 (area: 1 m2) is superposed and hot pressed to integrate (laminated filter medium 1), and the total basis weight is measured. The value obtained by subtracting the basis weights of the nonwoven fabric layer 1 and the nonwoven fabric layer 2 from the total basis weight is multiplied by the charge amount ratio of the functional particles 1, whereby the content of the functional particles 1 arranged in the laminated filter medium 1 per unit m$^2$ is calculated and this is used as a basis weight.

Next, a mixed powder 2 prepared by mixing and stirring functional particles 2 and an additive 2 such as a thermoplastic resin (binder) is scattered onto the laminated filter medium 1, and then another nonwoven fabric layer 3 (area: 1 m2) is superposed and hot pressed to integrate (multilayer filter medium 2). Then, the total basis weight is measured, and a value obtained by subtracting the basis weights of the laminate 1 and the nonwoven fabric layer 3 from the total basis weight is multiplied by the charge amount ratio of the functional particles 2, whereby the content of the functional particles 2 arranged in the multilayer filter medium 2 per unit m2 is calculated and this is used as a basis weight.

After that, this operation is repeated and thus the content per unit m2 of functional particles n arranged in a multilayer filter medium n (n is a natural number of 2 or more) is calculated and used as a basis weight. That is, a mixed powder n prepared by mixing and stirring functional particles n and an additive n such as a thermoplastic resin (binder) is scattered onto a laminated filter medium n−1, then another nonwoven fabric layer n+1 (area: 1 m2) is superposed and hot pressed to integrate (multilayer filter medium n), and the total basis weight is measured. The value obtained by subtracting the basis weights of the multilayer filter medium n−1 (not multilayer filter medium 1 but laminated body 1 only when n=2) and the nonwoven fabric layer n+1 from the total basis weight is multiplied by the charge amount ratio of the functional particles n, whereby the content of the functional particles n arranged in the multilayer filter medium n per unit m2 is calculated and this is used as a basis weight.

(10) Chemicals Detection Method

A nonwoven fabric layer was peeled off from the multilayer filter medium in the same manner as the above-described average particle diameter, and functional particles were taken out. After weighing 2 g of the functional particles, the particles were put in a 50 mL glass centrifuge tube and dissolved in 20 mL of acetonitrile/water (1:1). The prepared solution was filtered through a PTFE disk filter (0.45 μm), and the filtrate was used as a solution and subjected to liquid chromatography mass spectrometry (liquid chromatography system: Model: LC-20A manufactured by Shimadzu Corporation, column: Model: YMC Triart-PFP (3×150 mm, 3 μm) manufactured by YMC Co., Ltd., mass spectrometer: Model: API4000 manufactured by Sciex) under the condition involving the column temperature of 45° C., a flow rate of 0.3 mL/min, and an injection rate of 1 μL.

Production Examples

The functional particles, the electret nonwoven fabric layer, the sheet for improving the rigidity of the filter medium, and the multilayer filter medium used in examples and comparative examples were manufactured by the following methods.

(Functional Particles: Aldehyde Deodorant)

Functional particles A were used in which 7.2 parts by mass of adipic acid dihydrazide "CHEMCATCH 6000HS (manufactured by Otsuka Chemical Co., Ltd.)" as a chemical for aldehyde gas removal was affixed to 100 parts by mass of porous silica having an average particle diameter of 50 μm. Here, the average particle diameter of the functional particles A measured in the above (8) was 50 μm.

Functional particles A were used in which 7.2 parts by mass of adipic acid dihydrazide "CHEMCATCH 6000HS (manufactured by Otsuka Chemical Co., Ltd.)" as a chemical for aldehyde gas removal was affixed to 100 parts by mass of porous silica having an average particle diameter of 75 μm. Here, the average particle diameter of the functional particles A measured in the above (8) was 75 μm.

Functional particles A were used in which 7.2 parts by mass of adipic acid dihydrazide "CHEMCATCH 6000HS (manufactured by Otsuka Chemical Co., Ltd.)" as a chemical for aldehyde gas removal was affixed to 100 parts by mass of porous silica having an average particle diameter of 100 μm. Here, the average particle diameter of the functional particles A measured in the above (8) was 100 μm.

Functional particles B were used in which 7.2 parts by mass of adipic acid dihydrazide "CHEMCATCH 6000HS (manufactured by Otsuka Chemical Co., Ltd.)" as a chemical for aldehyde gas removal was affixed to 100 parts by mass of porous silica having an average particle diameter of 300 μm. Here, the average particle diameter of the functional particles B measured in the above (8) was 300 μm.

(Functional Particles: Organic Gas/Acidic Gas Deodorant)

Activated carbon having an average particle diameter of 75 μm was used as the functional particles B. Here, the average particle diameter of the functional particles B measured in the above average particle diameter [μm] (8) was 75 μm.

Activated carbon having an average particle diameter of 300 μm was used as the functional particles B. Here, the average particle diameter of the functional particles B measured in the above average particle diameter [μm] (8) was 300 μm.

(Functional Particles: Cation-Exchange Resin)

A cation-exchange resin having an average particle diameter of 75 μm was used as the functional particles A. Here, the average particle diameter of the functional particles A measured in the above average particle diameter [μm] (8) was 75 μm.

A cation-exchange resin having an average particle diameter of 300 μm was used as the functional particles A. Here, the average particle diameter of the functional particles A measured in the above average particle diameter [μm] (8) was 300 μm.

(Functional Particles: Acidic Gas Deodorant)

Functional particles B were used in which 20 parts by mass of potassium carbonate as a chemical for acidic gas removal was affixed to 100 parts by mass of activated carbon having an average particle diameter of 75 μm. Here, the average particle diameter of the functional particles B measured in the above average particle diameter [μm] (8) was 75 μm.

Functional particles B were used in which 20 parts by mass of potassium carbonate as a chemical for acidic gas removal was affixed to 100 parts by mass of activated carbon having an average particle diameter of 300 μm. Here, the average particle diameter of the functional particles B measured in the above average particle diameter [μm] (8) was 300 μm.

(Functional Particles: Alkaline Gas Deodorant)

Functional particles B were used in which 20 parts by mass of acetic acid as a chemical for alkali gas removal was affixed to 100 parts by mass of activated carbon having an average particle diameter of 75 μm. Here, the average particle diameter of the functional particles B measured in the above average particle diameter [μm] (8) was 75 μm.

Functional particles B were used in which 20 parts by mass of acetic acid as a chemical for alkali gas removal was affixed to 100 parts by mass of activated carbon having an average particle diameter of 300 μm. Here, the average particle diameter of the functional particles B measured in the above average particle diameter [μm] (8) was 300 μm.

(Electret Nonwoven Fabric Layer)

An electret-treated polypropylene melt-blown nonwoven fabric layer (fiber diameter: 2.6 pm, basis weight: 19.5 g/m2, collection efficiency: 99.975%, pressure drop: 33.3 Pa, thickness: 0.16 mm) was used.

(Nonwoven Fabric Layer for Improving Rigidity of Filter Medium (Hereinafter Referred to as "Sheet for Improving Rigidity"))

A nonwoven fabric layer (fiber diameter: 13 μm, basis weight: 25.3 g/m2, pressure drop: 0.8 Pa, thickness: 0.20 mm) containing glass fibers, polyvinyl alcohol fibers, and vinyl acetate resin in a mass ratio of 16:3:1 was used.

Examples, Comparative Examples

In the following description, in each Example and each Comparative Example except Comparative Examples 2 and 7, there is a step of superposing the next sheet for improving rigidity on a nonwoven fabric layer and further superposing a nonwoven fabric. The portion that is formed between layers in the first superposition is interlayer region 1, and the portion that is formed between layers in the second superposition is interlayer region 2.

Example 1

After scattering 25 g/m² of the above-described aldehyde deodorant having an average particle diameter of 50 μm and 7.5 g/m² of a low melting point polyethylene resin powder onto the above-described electret nonwoven fabric layer, a sheet for improving rigidity was superposed thereon, and 75 g/m² of the above-described aldehyde deodorant having an average particle diameter of 300 μm and 22.5 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium A was prepared. The multilayer filter medium A was cut out, and a part thereof was allowed to stand in an indoor environment at 25° C. and a humidity of 50% RH for one year to prepare a multilayer filter medium A' stored for one year.

Example 2

After scattering 50 g/m² of the above-described aldehyde deodorant having an average particle diameter of 50 μm and 15 g/m2 of a low melting point polyethylene resin powder onto the above-described electret nonwoven fabric layer, a sheet for improving rigidity was superposed thereon, and 50 g/m² of the above-described aldehyde deodorant having an average particle diameter of 300 μm and 15 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium B was prepared. The multilayer filter medium B was cut out, and a part thereof was allowed to stand in an indoor environment at 25° C. and a humidity of 50% RH for one year to prepare a multilayer filter medium B' stored for one year.

Example 3

After scattering 75 g/m² of the above-described aldehyde deodorant having an average particle diameter of 50 μm and 22.5 g/m2 of a low melting point polyethylene resin powder onto the above-described electret nonwoven fabric layer, a sheet for improving rigidity was superposed thereon, and 25 g/m² of the above-described aldehyde deodorant having an average particle diameter of 300 μm and 7.5 g/m2 of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium C was prepared. The multilayer filter medium C was cut out, and a part thereof was allowed to stand in an indoor environment at 25° C. and a humidity of 50% RH for one year to prepare a multilayer filter medium C' stored for one year.

Example 4

After scattering 25 g/m² of the above-described aldehyde deodorant having an average particle diameter of 75 μm and 7.5 g/m² of a low melting point polyethylene resin powder onto the above-described electret nonwoven fabric layer, a sheet for improving rigidity was superposed thereon, and 75 g/m² of the above-described aldehyde deodorant having an average particle diameter of 300 μm and 22.5 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium D was prepared. The multilayer filter medium D was cut out, and a part thereof was allowed to stand in an indoor environment at 25° C. and a humidity of 50% RH for one year to prepare a multilayer filter medium D' stored for one year.

Example 5

After scattering 50 g/m² of the above-described aldehyde deodorant having an average particle diameter of 75 μm and 15 g/m² of a low melting point polyethylene resin powder onto the above-described electret nonwoven fabric layer, a sheet for improving rigidity was superposed thereon, and 50 g/m² of the above-described aldehyde deodorant having an average particle diameter of 300 μm and 15 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium E was prepared. The multilayer filter medium E was cut out, and a part thereof was allowed to stand in an indoor environment at 25° C. and a humidity of 50% RH for one year to prepare a multilayer filter medium E' stored for one year.

Example 6

After scattering 75 g/m² of the above-described aldehyde deodorant having an average particle diameter of 75 μm and 22.5 g/m² of a low melting point polyethylene resin powder onto the above-described electret nonwoven fabric layer, a sheet for improving rigidity was superposed thereon, and 25 g/m² of the above-described aldehyde deodorant having an average particle diameter of 300 μm and 7.5 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium F was prepared. The multilayer filter medium F was cut out, and a part thereof was allowed to stand in an indoor environment at 25° C. and a humidity of 50% RH for one year to prepare a multilayer filter medium F' stored for one year.

Example 7

After scattering 25 g/m² of the above-described aldehyde deodorant having an average particle diameter of 100 μm and 7.5 g/m² of a low melting point polyethylene resin powder onto the above-described electret nonwoven fabric layer, a sheet for improving rigidity was superposed thereon, and 75 g/m² of the above-described aldehyde deodorant having an average particle diameter of 300 μm and 22.5 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium G was prepared. The multilayer filter medium G was cut out, and a part thereof was allowed to stand in an indoor environment at 25° C. and a humidity of 50% RH for one year to prepare a multilayer filter medium G' stored for one year.

Example 8

After scattering 50 g/m² of the above-described aldehyde deodorant having an average particle diameter of 100 μm and 15 g/m² of a low melting point polyethylene resin powder onto the above-described electret nonwoven fabric layer, a sheet for improving rigidity was superposed thereon, and 50 g/m² of the above-described aldehyde deodorant having an average particle diameter of 300 μm and 15 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium H was prepared. The multilayer filter medium H was cut out, and a part thereof was allowed to stand in an indoor environment at 25° C. and a humidity of 50% RH for one year to prepare a multilayer filter medium H' stored for one year.

Example 9

After scattering 75 g/m² of the above-described aldehyde deodorant having an average particle diameter of 100 μm and 22.5 g/m2 of a low melting point polyethylene resin powder onto the above-described electret nonwoven fabric layer, a sheet for improving rigidity was superposed thereon, and 25 g/m² of the above-described aldehyde deodorant having an average particle diameter of 300 μm and 7.5 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium I was prepared. The multilayer filter medium I was cut out, and a part thereof was allowed to stand in an indoor environment at 25° C. and a humidity of 50% RH for one year to prepare a multilayer filter medium I' stored for one year.

Example 10

After scattering 50 g/m² of the above-described cation-exchange resin having an average particle diameter of 75 μm and 15 g/m² of a low melting point polyethylene resin powder onto the above-described electret nonwoven fabric layer, a sheet for improving rigidity was superposed thereon, and 150 g/m² of the above-described activated carbon having an average particle diameter of 300 μm and 45 g/m² of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium J was prepared.

Example 11

After scattering 50 g/m² of the above-described aldehyde deodorant having an average particle diameter of 75 μm and 15 g/m2 of a low melting point polyethylene resin powder onto the above-described electret nonwoven fabric layer, a sheet for improving rigidity was superposed thereon and the low melting point polyethylene resin powder was melted by heating, and 150 g/m2 of the above-described activated carbon having an average particle diameter of 300 μm and 45 g/m2 of a low melting point polyethylene resin powder were scattered thereon. Furthermore, the above-mentioned electret nonwoven fabric layer was superposed thereon, and thus a multilayer filter medium K was prepared.

Example 12

After scattering 50 g/m2 of the above-described phosphoric acid-impregnated activated carbon having an average particle diameter of 75 μm and 15 g/m2 of a low melting point polyethylene resin powder onto the above-described electret nonwoven fabric layer, a sheet for improving rigidity was superposed thereon, and 150 g/m2 of the above-described potassium carbonate-impregnated activated carbon having an average particle diameter of 300 μm and 45 g/m2 of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium L was prepared.

Example 13

After scattering 50 g/m2 of the above-described potassium carbonate-impregnated activated carbon having an average particle diameter of 75 μm and 15 g/m2 of a low melting point polyethylene resin powder onto the above-described electret nonwoven fabric layer, a sheet for improving rigidity was superposed thereon, and 150 g/m$^2$ of the above-described phosphoric acid-impregnated activated carbon having an average particle diameter of 300 μm and 45 g/m$^2$ of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium M was prepared.

Example 14

After scattering 50 g/m$^2$ of the above-described aldehyde deodorant having an average particle diameter of 75 μm and 15 g/m2 of a low melting point polyethylene resin powder onto the above-described electret nonwoven fabric layer, a sheet for improving rigidity was superposed thereon, and 150 g/m$^2$ of the above-described potassium carbonate-impregnated activated carbon having an average particle diameter of 300 μm and 45 g/m2 of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium N was prepared.

Comparative Example 1

After scattering 50 g/m$^2$ of the above-described aldehyde deodorant having an average particle diameter of 75 μm and 15 g/m$^2$ of a low melting point polyethylene resin powder onto the above-described electret nonwoven fabric layer, a sheet for improving rigidity was superposed thereon, and 50 g/m$^2$ of the above-described aldehyde deodorant having an average particle diameter of 75 μm and 15 g/m$^2$ of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium O just after filter medium production was prepared. The multilayer filter medium O was cut out, and a part thereof was allowed to stand in an indoor environment at 25° C. and a humidity of 50% RH for one year to prepare a multilayer filter medium O' stored for one year.

Comparative Example 2

After scattering 100 g/m$^2$ of the above-described aldehyde deodorant having an average particle diameter of 75 μm and 25 g/m$^2$ of a low melting point polyethylene resin powder onto the above-described electret nonwoven fabric layer, a sheet for improving rigidity was superposed thereon, and 5 g/m$^2$ of a low melting point polyethylene resin powder was scattered each thereon (interlayer region 2). Furthermore, the above-mentioned electret nonwoven fabric layer was superposed thereon, and the low melting point resin powders located in the two interlayer regions were melted by heating to partially bond the adjacent layers, and thus a multilayer filter medium P just after filter medium production was prepared. The multilayer filter medium P was cut out, and a part thereof was allowed to stand in an indoor environment at 25° C. and a humidity of 50% RH for one year to prepare a multilayer filter medium P' stored for one year.

Comparative Example 3

After scattering 50 g/m$^2$ of the above-described aldehyde deodorant having an average particle diameter of 300 μm and 15 g/m$^2$ of a low melting point polyethylene resin powder onto the above-described electret nonwoven fabric layer, a sheet for improving rigidity was superposed thereon, and 50 g/m2 of the above-described aldehyde deodorant having an average particle diameter of 300 μm and 15 g/m$^2$ of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium Q just after filter medium production was prepared. The multilayer filter medium Q was cut out, and a part thereof was allowed to stand in an indoor environment at 25° C. and a humidity of 50% RH for one year to prepare a multilayer filter medium Q' stored for one year.

Comparative Example 4

After scattering 100 g/m$^2$ of the above-described aldehyde deodorant having an average particle diameter of 300 μm and 25 g/m$^2$ of a low melting point polyethylene resin powder onto the above-described electret nonwoven fabric layer, a sheet for improving rigidity was superposed thereon, and 5 g/m$^2$ of a low melting point polyethylene resin powder was scattered each thereon (interlayer region 2). Furthermore, the above-mentioned electret nonwoven fabric layer was superposed thereon, and the low melting point resin powders located in the two interlayer regions were melted by heating to partially bond the adjacent layers, and thus a multilayer filter medium R just after filter medium production was prepared. The multilayer filter medium R was cut out, and a part thereof was allowed to stand in an indoor environment at 25° C. and a humidity of 50% RH for one year to prepare a multilayer filter medium R' stored for one year.

Comparative Example 5

After scattering 25 g/m$^2$ of the above-described aldehyde deodorant having an average particle diameter of 75 μm, 75 g/m$^2$ of the above-described aldehyde deodorant having an average particle diameter of 300 μm, and 30 g/m$^2$ of a low melting point polyethylene resin powder onto the above-described electret nonwoven fabric layer, a sheet for improving rigidity was superposed thereon, and 5 g/m$^2$ of a low melting point polyethylene resin powder was scattered each thereon. Furthermore, the above-mentioned electret nonwoven fabric layer was superposed thereon, and the low melting point resin powders located in the two interlayer regions were melted by heating to partially bond the adjacent layers, and thus a layer filter medium S was prepared.

Comparative Example 6

After scattering 50 g/m$^2$ of the above-described cation-exchange resin having an average particle diameter of 300 μm and 15 g/m$^2$ of a low melting point polyethylene resin powder onto the above-described electret nonwoven fabric layer, a sheet for improving rigidity was superposed thereon, and 150 g/m$^2$ of the above-described activated carbon having an average particle diameter of 300 μm and 45 g/m$^2$ of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium T was prepared.

Comparative Example 7

After scattering 150 g/m$^2$ of the above-described activated carbon having an average particle diameter of 75 μm and 45 g/m$^2$ of a low melting point polyethylene resin powder onto the above-described electret nonwoven fabric layer, a sheet for improving rigidity was superposed thereon, and 50 g/m$^2$ of the above-described cation-exchange resin having an average particle diameter of 75 μm and 15 g/m$^2$ of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium U was prepared.

Comparative Example 8

After scattering 75 g/m$^2$ of the above-described potassium carbonate-impregnated activated carbon having an average particle diameter of 300 μm and 22.5 g/m$^2$ of a low melting point polyethylene resin powder onto the above-described electret nonwoven fabric layer, a sheet for improving rigidity was superposed thereon, and 150 g/m$^2$ of the above-described aldehyde deodorant having an average particle diameter of 300 μm and 45 g/m$^2$ of a low melting point polyethylene resin powder were scattered thereon. Furthermore, the above-mentioned electret nonwoven fabric layer was superposed thereon, and the low melting point resin powders located in the two interlayer regions were melted by heating to partially bond the adjacent layers, and thus a multilayer filter medium V was prepared.

Comparative Example 9

After scattering 50 g/m$^2$ of the above-described potassium carbonate-impregnated activated carbon having an average particle diameter of 75 μm (first functional particles), 150 g/m$^2$ of the above-described phosphoric acid-affixed char having an average particle diameter of 300 pm (second functional particles), and 60 g/m$^2$ of a low melting point polyethylene resin powder onto the above-described electret nonwoven fabric layer (interlayer region 1), a sheet for improving rigidity was superposed thereon, and 5 g/m$^2$ of a low melting point polyethylene resin powder were scattered each thereon. Furthermore, the above-mentioned electret nonwoven fabric layer was superposed thereon, and the low melting point resin powders located in the two interlayer regions were melted by heating to partially bond the adjacent layers, and thus a multilayer filter medium W was prepared.

Comparative Example 10

After scattering 50 g/m$^2$ of the above-described aldehyde deodorant having an average particle diameter of 75 μm (first functional particles), 150 g/m$^2$ of the above-described potassium carbonate-affixed char having an average particle diameter of 300 μm (second functional particles), and 30 g/m$^2$ of a low melting point polyethylene resin powder onto the above-described electret nonwoven fabric layer, a sheet for improving rigidity was superposed thereon, and 5 g/m$^2$ of a low melting point polyethylene resin powder were scattered each thereon. Furthermore, the above-mentioned electret nonwoven fabric layer was superposed thereon, and the low melting point resin powders located in the two interlayer regions were melted by heating to partially bond the adjacent layers, and thus a multilayer filter medium X just after filter medium production was prepared. For the samples obtained in Examples 1 to 14 and Comparative Examples 1 to 10, the above-described collection efficiency [%], pressure drop [Pa], deodorizing performance [%], and average particle diameter [μm] of each interlayer region were measured. The configurations and measurement results are summarized in Tables 1 to 6.

In Comparative Examples 2 and 7, the functional particles were densely packed in one interlayer region, so that the pressure drop was high. In Comparative Example 1, the deterioration of the functional particles A was promoted, and the aldehyde gas deodorizing performance after one year storage of the filter medium was remarkably deteriorated as compared with Examples 1 to 3. Further, in Comparative Examples 3 and 4, the deodorizing performance immediately after production was significantly inferior to that of Examples 2, 5 and 8. In Comparative Example 5, since the functional particles have a wide particle size distribution, the functional particles having a smaller particle diameter entered and were densely packed in the gaps formed by a plurality of functional particles having a larger particle diameter, resulting in a high pressure drop. In Comparative Example 6, since the particle diameter of the alkaline gas deodorant was large, the specific surface area was small and the ammonia gas deodorizing performance was deteriorated. In Comparative Example 8, since the particle diameter of the aldehyde gas deodorant was large, the specific surface area was small and the aldehyde gas deodorizing performance was deteriorated. In Comparative Example 9, since the acidic gas deodorant and the alkaline gas deodorant were in one interlayer region, the deodorant agents neutralized each other, and the deodorizing performance for acetic acid gas and ammonia gas was deteriorated. In Comparative Example 10, since the acidic gas deodorant and the aldehyde gas deodorant are in one interlayer region, the pH of the interlayer region where the acidic gas deodorant and the aldehyde gas deodorant were arranged was 10. Since the porous silica to which adipic acid dihydrazide used as an aldehyde gas deodorant was affixed has a property that the deodorizing performance is high at pH 3.0 to 7.5, the aldehyde gas deodorizing performance was deteriorated.

TABLE 1

| | Example 1 | Example 2 | Example 3 | Example 4 | Example 5 | Example 6 | Example 7 | Example 8 | Example 9 |
|---|---|---|---|---|---|---|---|---|---|
| Type of functional particles (interlayer region 1) | Aldehyde deodorant (Chemical-affixed porous silica) | Same as the left | Same as the left | Same as the left | Same as the left | Same as the left | Same as the left | Same as the left | Same as the left |
| Affixed chemical of functional particles (interlayer region 1) | Adipic acid dihydrazide | Same as the left | Same as the left | Same as the left | Same as the left | Same as the left | Same as the left | Same as the left | Same as the left |
| Average particle diameter (μm) (interlayer region 1) | 50 | 50 | 50 | 75 | 75 | 75 | 100 | 100 | 100 |
| Type of functional particles (interlayer region 2) | Aldehyde deodorant (Chemical-affixed porous silica) | Same as the left | Same as the left | Same as the left | Same as the left | Same as the left | Same as the left | Same as the left | Same as the left |
| Affixed chemical of functional particles (interlayer region 2) | Adipic acid dihydrazide | Same as the left | Same as the left | Same as the left | Same as the left | Same as the left | Same as the left | Same as the left | Same as the left |
| Average particle diameter (μm) (interlayer region 2) | 300 | 300 | 300 | 300 | 300 | 300 | 300 | 300 | 300 |
| Basis weight of functional particles (g/m²) (Interlayer 1) | 25 | 50 | 75 | 25 | 50 | 75 | 25 | 50 | 75 |
| Functional particles Low melting point powder resin | 7.5 | 15 | 22.5 | 7.5 | 15 | 22.5 | 7.5 | 15 | 22.5 |
| Basis weight of functional particles (g/m²) (Interlayer 2) | 75 | 50 | 25 | 75 | 50 | 25 | 75 | 50 | 25 |
| Functional Particles Low melting point particles | 22.5 | 15 | 7.5 | 22.5 | 15 | 7.5 | 22.5 | 15 | 7.5 |
| Pressure loss (Pa) | 71 | 73 | 85 | 70 | 73 | 84 | 70 | 72 | 88 |
| Collection efficiency (%) of filter medium | 99.988 | 99.989 | 99.986 | 99.987 | 99.989 | 99.992 | 99.989 | 99.987 | 99.981 |
| Acetaldehyde adsorption rate, adsorption capacity | Just after production | Initial removal efficiency (%) | 80.2 | 87.5 | 89.1 | 80.6 | 87.6 | 88.6 | 77.1 | 83.1 | 88.5 |
| | | Removal efficiency (%) 12 minutes after addition | 48.1 | 57.4 | 58.4 | 47.3 | 56.3 | 58.2 | 53.1 | 56.7 | 57.1 |
| | | Adsorption capacity (g/m²) | 2.85 | 3.21 | 3.36 | 2.88 | 3.23 | 3.33 | 2.76 | 3.15 | 3.22 |
| | 1 year after production | Initial removal efficiency (%) | 60.1 | 59.2 | 53.1 | 62.2 | 59.6 | 55.2 | 60.3 | 59.7 | 56.1 |
| | | Removal efficiency (%) 12 minutes after addition | 40.2 | 44.1 | 33.4 | 42.1 | 39.9 | 37.6 | 41.1 | 44.7 | 38.9 |
| | | Adsorption capacity (g/m²) | 1.76 | 1.60 | 1.51 | 1.78 | 1.61 | 1.55 | 1.77 | 1.62 | 1.61 |

TABLE 2

|  |  | Example 10 | Example 11 | Example 12 |
|---|---|---|---|---|
| Type of functional particles (interlayer 1) | | Alkaline gas deodorant (Cation-exchange resin) | Aldehyde deodorant (Chemical-affixed porous silica) | Alkaline gas deodorant (Chemical-affixed activated carbon) |
| Affixed chemical of functional particles (interlayer 1) | | None | Adipic acid dihydrazide | Phosphoric acid |
| Average particle diameter (µm) (interlayer 1) | | 75 | 75 | 75 |
| Type of functional particles (interlayer 2) | | Organic gas/acidic gas deodorant (Activated carbon) | Organic gas/acidic gas deodorant (Activated carbon) | Acidic gas deodorant (Chemical-affixed activated carbon) |
| Affixed chemical of functional particles (interlayer 2) | | None | None | Potassium carbonate |
| Average particle diameter (µm) (interlayer 2) | | 300 | 300 | 300 |
| Basis weight of functional particles (g/m²) (Interlayer 1) | Functional particles | 50 | 50 | 50 |
| | Low melting point powder resin | 15 | 15 | 15 |
| Basis weight of functional particles (g/m²) (Interlayer 2) | Functional particles | 150 | 150 | 150 |
| | Low melting point powder resin | 45 | 45 | 45 |
| Pressure loss (Pa) and collection efficiency (%) of filter medium | Pressure loss (Pa) | 74 | 75 | 73 |
| | Collection efficiency (%) | 99.987 | 99.988 | 99.988 |
| Gas adsorption rate and adsorption capacity just after production | Acetaldehyde Removal efficiency (%) 2 minutes after addition | 45.2 | 87.8 | 36.2 |
| | Removal efficiency (%) 12 minutes after addition | 12.8 | 57.8 | 6.5 |
| | Adsorption capacity (g/m²) | 0.26 | 1.21 | 0.23 |
| | Acetic acid Removal efficiency (%) 2 minutes after addition | 84.7 | 86.8 | 82.4 |
| | Removal efficiency (%) 12 minutes after addition | 78.7 | 78.3 | 78.6 |
| | Adsorption capacity (g/m²) | 44.8 | 43.4 | 53.2 |
| | Ammonia Removal efficiency (%) 2 minutes after addition | 82.1 | 46.2 | 86.6 |
| | Removal efficiency (%) 12 minutes after addition | 64.3 | 16.8 | 25.4 |
| | Adsorption capacity (g/m²) | 5.7 | 0.76 | 1.67 |
| | Toluene Removal efficiency (%) 2 minutes after addition | 83.6 | 86.6 | 82.4 |
| | Removal efficiency (%) 12 minutes after addition | 78.1 | 78.3 | 53.5 |
| | Adsorption capacity (g/m²) | 54.9 | 56.6 | 44.6 |

TABLE 3

|  |  | Example 13 | Example 14 |
|---|---|---|---|
| Type of functional particles (interlayer 1) | | Acidic gas deodorant (Chemical-affixed activated carbon) | Aldehyde deodorant (Chemical-affixed porous silica) |
| Affixed chemical of functional particles (interlayer 1) | | Potassium carbonate | Adipic acid dihydrazide |
| Average particle diameter (µm) (interlayer 1) | | 75 | 75 |
| Type of functional particles (interlayer 2) | | Alkaline gas deodorant (Chemical-affixed activated carbon) | Acidic gas deodorant (Chemical-affixed activated carbon) |
| Affixed chemical of functional particles (interlayer 2) | | Phosphoric acid | Potassium carbonate |
| Average particle diameter (µm) (interlayer 2) | | 300 | 300 |
| Basis weight of functional particles (g/m²) (Interlayer 1) | Functional particles | 50 | 50 |
| | Low melting point powder resin | 15 | 15 |
| Basis weight of functional particles (g/m²) (Interlayer 2) | Functional particles | 150 | 150 |
| | Low melting point powder resin | 45 | 45 |
| Pressure loss (Pa) and collection efficiency (%) of filter medium | Pressure loss (Pa) | 75 | 75 |
| | Collection efficiency (%) | 99.986 | 99.990 |
| Gas adsorption rate and adsorption capacity just after production | Acetaldehyde Removal efficiency (%) 2 minutes after addition | 35.5 | 88.7 |
| | Removal efficiency (%) 12 minutes after addition | 6.7 | 56.8 |
| | Adsorption capacity (g/m²) | 0.24 | 1.20 |
| | Acetic acid Removal efficiency (%) 2 minutes after addition | 93.4 | 83.4 |
| | Removal efficiency (%) 12 minutes after addition | 75.5 | 78.6 |
| | Adsorption capacity (g/m²) | 34.2 | 53.4 |
| | Ammonia Removal efficiency (%) 2 minutes after addition | 85.4 | 45.6 |
| | Removal efficiency (%) 12 minutes after addition | 57.5 | 10.4 |
| | Adsorption capacity (g/m²) | 4.76 | 0.46 |
| | Toluene Removal efficiency (%) 2 minutes after addition | 83.4 | 76.4 |
| | Removal efficiency (%) 12 minutes after addition | 55.7 | 45.2 |
| | Adsorption capacity (g/m²) | 36.50 | 46.7 |

TABLE 4

|  |  | Comparative Example 1 | Comparative Example 2 | Comparative Example 3 | Comparative Example 4 |
|---|---|---|---|---|---|
| Type of functional particles (interlayer region 1) | | Aldehyde deodorant (Chemical-affixed porous silica) | Same as the left | Same as the left | Same as the left |
| Affixed chemical of functional particles (interlayer region 1) | | Adipic acid dihydrazide | Same as the left | Same as the left | Same as the left |
| Average particle diameter (μm) (interlayer region 1) | | 75 | 75 | 300 | 300 |
| Type of functional particles (interlayer region 2) | | Aldehyde deodorant (Chemical-affixed porous silica) | Same as the left | Same as the left | Same as the left |
| Affixed chemical of functional particles (interlayer region 2) | | Adipic acid dihydrazide | Same as the left | Same as the left | Same as the left |
| Average particle diameter (μm) (interlayer region 2) | | 75 | 75 | 300 | 300 |
| Basis weight of functional particles (g/m²) (Interlayer 1) | Functional particles | 50 | 100 | 50 | 100 |
|  | Low melting point powder resin | 15 | 25 | 15 | 25 |
| Basis weight of functional particles (g/m²) (Interlayer 2) | Functional particles | 50 | 0 | 50 | 0 |
|  | Low melting point powder resin | 15 | 5 | 15 | 5 |
| Pressure loss (Pa) and collection efficiency (%) of filter medium | Pressure loss (Pa) | 83 | 110 | 70 | 85 |
|  | Collection efficiency (%) | 99.988 | 99.991 | 99.993 | 99.981 |
| Acetaldehyde adsorption rate, adsorption capacity | Just after production | | | | |
|  | Initial removal efficiency (%) | 90.7 | 89.1 | 72.5 | 72.8 |
|  | Removal efficiency (%) 12 minutes after addition | 64.3 | 63.1 | 32.1 | 33.0 |
|  | Adsorption capacity (g/m²) | 3.53 | 3.50 | 2.08 | 2.09 |
|  | 1 year after production | | | | |
|  | Initial removal efficiency (%) | 43.7 | 44.7 | 62.6 | 62.5 |
|  | Removal efficiency (%) 12 minutes after addition | 25.1 | 26.1 | 45.7 | 45.9 |
|  | Adsorption capacity (g/m²) | 1.11 | 1.21 | 1.88 | 1.90 |

TABLE 5

|  |  | Comparative Example 5 | Comparative Example 6 | Comparative Example 7 | Comparative Example 8 |
|---|---|---|---|---|---|
| Type of functional particles (interlayer region 1) | | Aldehyde deodorant (Chemical-affixed porous silica) | Organic gas/acidic gas deodorant (Activated carbon) | Organic gas/acidic gas deodorant (Activated carbon) | Acidic gas deodorant (Chemical-affixed activated carbon) |
| Affixed chemical of functional particles (interlayer region 1) | | Adipic acid dihydrazide | None | None | Potassium carbonate |
| Average particle diameter (μm) (interlayer region 1) (Interlayer region 2) | | 85 | 300 | 75 | 300 |
| Type of functional particles (interlayer region 2) | | — | Alkaline gas deodorant | Alkaline gas deodorant | Aldehyde gas deodorant |
| Affixed chemical of functional particles (interlayer region 2) | | — | Cation-exchange resin | Cation-exchange resin | Adipic acid dihydrazide |
| Average particle diameter (μm) (interlayer region 2) | | — | 300 | 75 | 300 |
| Basis weight of functional particles (g/m²) (Interlayer region 1) | Functional particles | 100 | 150 | 150 | 75 |
|  | Low melting point powder resin | 30 | 45 | 45 | 22.5 |
| Basis weight of functional particles (g/m²) (Interlayer region 2) | Functional particles | — | 50 | 50 | 150 |
|  | Low melting point powder resin | 5 | 15 | 15 | 45 |
| Pressure loss (Pa) and collection efficiency (%) of filter medium | Pressure loss (Pa) | 92 | 68 | 118 | 65 |
|  | Collection efficiency (%) | 99.987 | 99.988 | 99.988 | 99.987 |
| Gas adsorption rate and adsorption capacity just after production | Acetaldehyde | | | | |
|  | Removal efficiency (%) 2 minutes after addition | 92.4 | 44.2 | 74.3 | 73.8 |
|  | Removal efficiency (%) 12 minutes after addition | 75.4 | 11.8 | 14.3 | 45.9 |
|  | Adsorption capacity (g/m²) | 1.96 | 0.28 | 0.37 | 1.48 |
|  | Acetic acid | | | | |
|  | Removal efficiency (%) 2 minutes after addition | 56.4 | 85.3 | 93.2 | 86.4 |
|  | Removal efficiency (%) 12 minutes after addition | 6.5 | 77.2 | 83.1 | 46.5 |
|  | Adsorption capacity (g/m²) | 1.51 | 43.61 | 43.70 | 25.60 |
|  | Ammonia | | | | |
|  | Removal efficiency (%) 2 minutes after addition | 54.6 | 46.3 | 86.2 | 56.4 |
|  | Removal efficiency (%) 12 minutes after addition | 4.5 | 35.6 | 67.2 | 4.7 |
|  | Adsorption capacity (g/m²) | 1.62 | 5.62 | 5.41 | 2.89 |
|  | Toluene | | | | |
|  | Removal efficiency (%) 2 minutes after addition | 53.2 | 86.7 | 93.0 | 78.2 |
|  | Removal efficiency (%) 12 minutes after addition | 4.8 | 78.8 | 83.2 | 46.4 |
|  | Adsorption capacity (g/m²) | 1.57 | 56.21 | 56.28 | 35.90 |

TABLE 6

| | | | Comparative Example 9 | Comparative Example 10 |
|---|---|---|---|---|
| Type of first functional particles (interlayer region 1) | | | Acidic gas deodorant (Chemical-affixed activated carbon) | Aldehyde deodorant (Chemical-affixed porous silica) |
| Affixed chemical of first functional particles (interlayer region 1) | | | Potassium carbonate | Adipic acid dihydrazide |
| Type of second functional particles (interlayer region 1) | | | Alkaline gas deodorant (Chemical-affixed activated carbon) | Acidic gas deodorant (Chemical-affixed activated carbon) |
| Affixed chemical of second functional particles (interlayer region 1) | | | Phosphoric acid | Potassium carbonate |
| Average particle diameter (μm) (interlayer region 1) | | | 87 | 83 |
| (Interlayer region 2) | | | | |
| Type of functional particles (interlayer region 2) | | | — | — |
| Affixed chemical of functional particles (interlayer region 2) | | | — | — |
| Average particle diameter (μm) (interlayer region 2) | | | — | — |
| Basis weight of functional particles (g/m$^2$) (Interlayer region 1) | | Functional particles | 200 | 200 |
| | | Low melting point powder resin | 60 | 60 |
| Basis weight of functional particles (g/m$^2$) (Interlayer region 2) | | Functional particles | — | — |
| | | Low melting point powder resin | 5 | 5 |
| Pressure loss (Pa) and collection efficiency (%) of filter medium | | Pressure loss (Pa) | 125 | 115 |
| | | Collection efficiency (%) | 99.990 | 99.987 |
| Gas adsorption rate and adsorption capacity just after production | Acetaldehyde | Removal efficiency (%) 2 minutes after addition | 39.8 | 56.2 |
| | | Removal efficiency (%) 12 minutes after addition | 7 | 25.1 |
| | | Adsorption capacity (g/m$^2$) | 0.28 | 0.57 |
| | Acetic acid | Removal efficiency (%) 2 minutes after addition | 64.5 | 85.6 |
| | | Removal efficiency (%) 12 minutes after addition | 36.1 | 80.2 |
| | | Adsorption capacity (g/m$^2$) | 17.4 | 52.4 |
| | Ammonia | Removal efficiency (%) 2 minutes after addition | 34.9 | 48.9 |
| | | Removal efficiency (%) 12 minutes after addition | 10.2 | 11.4 |
| | | Adsorption capacity (g/m$^2$) | 2.75 | 0.45 |
| | Toluene | Removal efficiency (%) 2 minutes after addition | 86.8 | 78.7 |
| | | Removal efficiency (%) 12 minutes after addition | 57.9 | 46.5 |
| | | Adsorption capacity (g/m$^2$) | 36.6 | 45.9 |

The multilayer filter medium of the present invention can suppress the deterioration of its deodorizing performance after long-term storage of the filter medium and is superior in deodorizing performance and exhibits low pressure drop. The multilayer filter medium can be suitably used for a filter for air cleaners, a cabin filter for automobiles, or the like.

The invention claimed is:

1. A multilayer filter medium comprising three or more nonwoven fabric layers superposed together and having two or more interlayer regions each formed by two adjacent layers of the nonwoven fabric layers, wherein
   a first interlayer region of the interlayer regions contains functional particles A having an average particle diameter of 50 to 100 μm, and
   a second interlayer region selected from the interlayer regions excluding the first interlayer region contains functional particles B having an average particle diameter of 150 to 500 μm.

2. The multilayer filter medium according to claim 1, wherein
   a basis weight of the functional particles A in the first interlayer region is 20 to 80 g/m$^2$, and
   a basis weight of the functional particles B in the second interlayer region is 20 to 600 g/m$^2$.

3. The multilayer filter medium according to claim 1, wherein
   one of the functional particles A and the functional particles B is functional particles having acidic gas adsorption capability, and
   the other of the functional particles A and the functional particles B is functional particles having basic gas adsorption capability.

4. The multilayer filter medium according to claim 1, wherein at least one layer of the three or more nonwoven fabric layers is charged nonwoven fabric.

5. The multilayer filter medium according to claim 1 which has a collection efficiency of 99.97% or more for particles having an average particle diameter of 0.3 μm.

6. The multilayer filter medium according to claim 1, wherein at least one of the functional particles A and the functional particles B chemically adsorbs volatile organic compound gas.

7. The multilayer filter medium according to claim 1, wherein at least one of the functional particles A and the functional particles B selectively and chemically adsorbs aldehyde gas.

8. An air filter comprising the multilayer filter medium according to claim 1.

9. A method for manufacturing the multilayer filter medium according to claim 1, comprising:
   a step of arranging the functional particles A on a surface of a first nonwoven fabric layer selected from among the nonwoven fabric layers;
   a step of arranging the functional particles B on a surface of a second nonwoven fabric layer selected from among the nonwoven fabric layers; and
   a step of superposing three or more nonwoven fabric layers.

10. The multilayer filter medium according to claim 1, wherein the two adjacent layers of the nonwoven fabric layers are partially bonded by scattered resin located in the interlayer regions.

11. The multilayer filter medium according to claim 2, wherein the two adjacent layers of the nonwoven fabric layers are partially bonded by scattered resin located in the interlayer regions.

* * * * *